(12) United States Patent
Uotila et al.

(10) Patent No.: US 6,780,317 B1
(45) Date of Patent: Aug. 24, 2004

(54) METHOD OF PURIFYING WATER, SUITABLE BACTERIA FOR THE METHOD AND USE THEREOF

(75) Inventors: Jussi Uotila, Saarenkylä (FI); Gennadi Zaitsev, Rovaniemi (FI)

(73) Assignee: Oy Clewer Ltd, Saarenkyla (FI)

( * ) Notice: Subject to any disclaimer, the term of this patent is extended or adjusted under 35 U.S.C. 154(b) by 283 days.

(21) Appl. No.: 10/030,920

(22) PCT Filed: Jul. 6, 2000

(86) PCT No.: PCT/FI00/00642
§ 371 (c)(1),
(2), (4) Date: May 13, 2002

(87) PCT Pub. No.: WO01/04060
PCT Pub. Date: Jan. 18, 2001

(30) Foreign Application Priority Data

Jul. 12, 1999 (FI) .................................................. 991595

(51) Int. Cl.[7] .............................. C02F 3/00; C12N 1/20
(52) U.S. Cl. ...................... 210/601; 210/616; 210/192; 210/542; 210/629; 435/180; 435/252.4; 435/252.5; 435/253.3; 435/252.1
(58) Field of Search ........................ 210/601, 615–617, 210/192, 542, 189, 629; 435/180, 252.4, 252.5, 252.3, 252.1

(56) References Cited

U.S. PATENT DOCUMENTS

| | | | |
|---|---|---|---|
| 4,317,885 A | 3/1982 | Blair et al. | |
| 5,679,568 A | 10/1997 | Imamura et al. | |
| 6,309,871 B1 * | 10/2001 | Outtrup et al. | ............. 435/202 |

FOREIGN PATENT DOCUMENTS

| | | |
|---|---|---|
| EP | 0530859 | 3/1993 |
| EP | 0 915 061 | 5/1999 |
| WO | WO 8805334 | 7/1988 |
| WO | WO 9405866 | 3/1994 |

OTHER PUBLICATIONS

O.M. Väisänen et al., "Structure and Composition of Biological Slimes on Paper and Board Machines", *Applied and Environmental Microbiology*, vol. 60, No. 2, Feb. 1994, pp. 641–653.

* cited by examiner

*Primary Examiner*—Chester T. Barry
(74) *Attorney, Agent, or Firm*—Young & Thompson

(57) ABSTRACT

A method of purifying waste water biologically by using three particularly suitable bacteria: Bacillus sp. DT-1, *Pseudomonas azelaica*, DT-2, and/or Rhizobus sp. DT-5, or mixed populations thereof. The invention further relates to the bacteria and the mixed populations and use thereof in purifying waste water. The invention further relates to a bioreactor including the bacteria.

19 Claims, 10 Drawing Sheets

Fig. 2b

| RT | Area | Ar/Ht | Respon | ECL | Name | % Named | Total Amnt | Nbr Ref | ECL Deviation | Ref ECL Shift | Comment 1 | Comment 2 |
|---|---|---|---|---|---|---|---|---|---|---|---|---|
| 1.536 | 308581200 | 0.027 | . | 7.025 | SOLVENT PEAK | . | . | . | . | . | . | . |
| 1.847 | 17778 | 0.003 | . | 7.607 | . | . | . | . | . | . | < min rt | . |
| 4.110 | 1440 | 0.028 | 1.084 | 11.607 | 12:0 ISO | . | . | . | . | . | < min rt | . |
| 4.450 | 606 | 0.031 | 1.069 | 12.000 | 12:0 | . | . | . | . | . | ECL deviates -0.001 | Reference 0.003 |
| 5.110 | 10566 | 0.030 | 1.047 | 12.612 | 13:0 ISO | . | . | . | . | . | ECL deviates -0.000 | Reference 0.004 |
| 5.216 | 1182 | 0.033 | 1.044 | 12.702 | 13:0 ANTEISO | . | . | . | . | . | ECL deviates 0.000 | Reference 0.003 |
| 6.349 | 8064 | 0.033 | 1.014 | 13.618 | 14:0 ISO | . | . | . | . | . | ECL deviates 0.001 | Reference 0.004 |
| 6.049 | 3396 | 0.039 | 1.003 | 14.000 | 14:0 | . | . | . | . | . | ECL deviates -0.000 | Reference 0.002 |
| 7.774 | 18304 | 0.037 | 0.986 | 14.622 | 15:0 ISO | . | . | . | . | . | ECL deviates -0.000 | Reference 0.002 |
| 7.900 | 3624 | 0.038 | 0.984 | 14.712 | 15:0 ANTEISO | . | . | . | . | . | ECL deviates 0.001 | Reference 0.003 |
| 8.732 | 684 | 0.042 | . | 15.245 | . | . | . | . | . | . | ECL deviates 0.001 | Reference 0.003 |
| 8.964 | 1980 | 0.040 | 0.968 | 15.308 | 16:1 w7c alcohol | . | . | . | . | . | ECL deviates 0.002 | . |
| 9.117 | 3660 | 0.038 | 0.965 | 15.493 | Sum In Feature 3 | . | . | . | . | . | ECL deviates 0.001 | 16:1 ISO I/14:0 30 |
| 9.345 | 8022 | 0.044 | 0.962 | 15.624 | 16:0 ISO | . | . | . | . | . | ECL deviates -0.002 | Reference -0.001 |
| 9.562 | 582 | 0.039 | 0.959 | 15.758 | 16:1 w1c | . | . | . | . | . | ECL deviates 0.001 | . |
| 9.722 | 10494 | 0.040 | 0.957 | 15.857 | Sum In Feature 4 | . | . | . | . | . | ECL deviates 0.010 | 15:0 ISO 2OH/16:1w |
| 9.953 | 4800 | 0.040 | 0.954 | 15.999 | 16:0 | . | . | . | . | . | ECL deviates -0.001 | Reference 0.001 |
| 10.322 | 1500 | 0.038 | 0.950 | 16.210 | 15:0 2OH | . | . | . | . | . | ECL deviates 0.001 | . |
| 10.609 | 4914 | 0.041 | 0.946 | 16.387 | ISO 17:1 w10c | . | . | . | . | . | ECL deviates 0.000 | . |
| 10.735 | 4188 | 0.043 | 0.945 | 16.462 | ISO 17:1 w5c | . | . | . | . | . | ECL deviates 0.001 | . |
| 10.870 | 660 | 0.035 | 0.943 | 16.541 | 17:1 ANTEISO A | . | . | . | . | . | ECL deviates 0.000 | . |
| 11.018 | 6588 | 0.040 | 0.941 | 16.629 | 17:0 ISO | . | . | . | . | . | ECL deviates 0.000 | Reference 0.002 |
| 11.176 | 780 | 0.040 | 0.940 | 16.722 | 17:0 ANTEISO | . | . | . | . | . | ECL deviates 0.000 | Reference 0.002 |
| 13.379 | 624 | 0.044 | 0.918 | 17.001 | 18:0 | . | . | . | . | . | ECL deviates 0.001 | Reference 0.003 |
| ****** | . | . | . | . | SUMMED FEATURE 3 | . | . | . | . | . | 12:0 ALDE ? | unknown 10.928 |
| ****** | . | . | . | . | . | . | . | . | . | . | 16:1 ISO I/14:0 3OH | 14:0 3OH/16:1 ISO |
| ****** | 3660 | . | . | . | SUMMED FEATURE 4 | . | . | . | . | . | 16:1 w7c/15 iso 2OH | 15:0 ISO 2OH/16:1w |

| Solvent Ar. | Total Area | Named Area | % Named | Total Amnt | Nbr Ref | ECL Deviation | Ref ECL Shift |
|---|---|---|---|---|---|---|---|
| 308581200 | 96738 | 96054 | 99.29 | 94302 | 13 | 0.002 | 0.003 |

```
        TSBA (Rev 3.90) Bacillus . . . . . . . . . . . . . . 0.265 (Bacillus cereus group)
                        B. thuringiensis . . . . . . . . . . . 0.265 (Bacillus cereus group)
                        B. cereus . . . . . . . . . . . . . . 0.160

CLIN (Rev 3.90) * NO MATCH *
```

Fig. 3b

| RT | Area | Ar/Ht | Respon | ECL | Name | % | Comment 1 | Comment 2 |
|---|---|---|---|---|---|---|---|---|
| 1.489 | 150156 | 0.015 | . | 6.962 | SOLVENT PEAK | . | < min rt | |
| 1.520 | 274442400 | 0.026 | . | 7.029 | . | . | < min rt | |
| 3.915 | 10338 | 0.027 | 1.094 | 11.422 | 10:0 3OH | 2.95 | ECL deviates -0.001 | Reference 0.000 |
| 4.411 | 6870 | 0.030 | 1.071 | 11.999 | 12:0 | 1.92 | ECL deviates -0.001 | |
| 4.511 | 400 | 0.031 | 1.067 | 12.091 | 11:0 ISO 3OH | 0.11 | ECL deviates 0.001 | |
| 5.730 | 16770 | 0.032 | 1.028 | 13.177 | 12:0 2OH | 4.50 | ECL deviates -0.001 | |
| 6.092 | 14094 | 0.034 | 1.019 | 13.455 | 12:0 3OH | 3.75 | ECL deviates -0.000 | |
| 6.566 | 558 | 0.035 | . | 13.818 | . | . | . | |
| 6.802 | 2136 | 0.034 | 1.002 | 13.999 | 14:0 | 0.56 | ECL deviates -0.001 | Reference -0.001 |
| 7.727 | 846 | 0.041 | 0.984 | 14.624 | 15:0 ISO | 0.22 | ECL deviates 0.003 | Reference 0.002 |
| 8.208 | 630 | 0.045 | 0.974 | 15.002 | 15:0 | 0.16 | ECL deviates 0.002 | Reference 0.002 |
| 9.603 | 86670 | 0.040 | 0.955 | 15.816 | Sum In Feature 4 | 21.61 | ECL deviates -0.001 | 16:1 w7c/15 iso 2OH |
| 9.754 | 720 | 0.037 | 0.953 | 15.909 | 16:1 w5c | 0.18 | ECL deviates 0.001 | |
| 9.897 | 85084 | 0.040 | 0.951 | 15.998 | 16:0 | 21.32 | ECL deviates -0.002 | Reference -0.002 |
| 10.962 | 1596 | 0.042 | 0.938 | 16.629 | 17:0 ISO | 0.39 | ECL deviates -0.000 | Reference -0.001 |
| 11.236 | 984 | 0.043 | 0.935 | 16.791 | 17:1 w8a | 0.24 | ECL deviates -0.001 | |
| 11.399 | 6552 | 0.044 | 0.933 | 16.887 | 17:0 CYCLO | 1.60 | ECL deviates -0.001 | Reference -0.001 |
| 11.586 | 744 | 0.045 | 0.931 | 16.998 | 17:0 | 0.18 | ECL deviates -0.002 | Reference -0.002 |
| 13.012 | 163326 | 0.045 | 0.918 | 17.824 | Sum In Feature 7 | 39.14 | ECL deviates -0.001 | 18:1 w9c/w12t/w7a |
| 13.177 | 570 | 0.054 | 0.916 | 17.919 | 18:1 w5a | 0.14 | ECL deviates 0.000 | Reference 0.000 |
| 13.317 | 2106 | 0.042 | 0.915 | 18.001 | 18:0 | 0.50 | ECL deviates 0.001 | Reference 0.000 |
| 14.873 | 2220 | 0.046 | 0.904 | 18.901 | 19:0 CYCLO w8a | 0.32 | ECL deviates 0.001 | |
| ****** | 86670 | . | . | . | SUMMED FEATURE 4 | 21.61 | 16:1 w7c/15 iso 2OH | 18:1 w7c/w9t/w12t |
| ****** | 163326 | . | . | . | SUMMED FEATURE 7 | 39.14 | 18:1 w9t/w12t | 18:1 w12t/w9t/w7c |

| Solvent Ac | Total Area | Named Area | % Named | Total Amnt | Nbr Ref | ECL Deviation | Ref ECL Shift |
|---|---|---|---|---|---|---|---|
| 274442400 | 404022 | 403464 | 99.86 | 382931 | 10 | 0.001 | 0.002 |

TSBA [Rev 3.90]   Pseudomonas
    P. aeruginosa    0.700
    Flavimonas    0.700
    F. oryzihabitans    0.477 (Pseudomonas VE2)
    Chryseomonas    0.477 (Pseudomonas VE2)
    C. luteola    0.387 (Pseudomonas VE1)
        0.307 (Pseudomonas VE1)

CLIN [Rev 3.90]   Pseudomonas
    P. aeruginosa    0.339
    P. stutzeri    0.339
    Chryseomonas    0.242
    C. luteola    0.322 ("Pseudomonas VE1")
    Flavimonas    0.322 ("Pseudomonas VE1")
    F. oryzihabitans    0.205 (Pseudomonas VE2)

Fig. 4

| RT | Area | Ar/Ht Respon | RCL | Name | % | Comment 1 | Comment 2 |
|---|---|---|---|---|---|---|---|
| 1.665 | 243677184 | 0.032 | 7.032 | SOLVENT PEAK | | < min rt | |
| 1.946 | 536 | 0.030 | 7.563 | | | < min rt | |
| 10.502 | 1080 | 0.061 | 15.815 | Sum In Feature 4 | 0.81 | ECL deviates -0.002 | 16:1 w7c/15 iso 2OH |
| 10.614 | 9496 | 0.049 | 15.999 | 16:0 | 7.07 | ECL deviates -0.001 | Reference -0.001 |
| 11.924 | 6120 | 0.051 | 16.631 | 17:0 ISO | 4.50 | ECL deviates 0.002 | Reference 0.002 |
| 13.651 | 3040 | 0.058 | 17.606 | | | | |
| 14.043 | 113192 | 0.051 | 17.825 | Sum In Feature 7 | 85.92 | ECL deviates -0.000 | 18:1 w9c/w12t/w7c |
| 14.354 | 2376 | 0.050 | 17.999 | 18:0 | 1.71 | ECL deviates -0.001 | Reference -0.001 |
| 14.498 | 4160 | 0.055 | 18.081 | | | | |
| 14.615 | 2272 | 0.088 | 18.147 | | | | |
| ****** | 1080 | | | SUMMED FEATURE 4 | 0.81 | 16:1 w7c/15 iso 2OH | 15:0 ISO 2OH/16:1w7c |
| ****** | 119192 | | | SUMMED FEATURE 7 | 85.92 | 18:1 w7c/w9t/w12t | 18:1 w9c/w12t/w7c |
| ****** | | | | | | 18:1 w12t/w9t/w7c | |

| Solvent Ar | Total Area | Named Area | % Named | Total Amnt | Nbr Ref | ECL Deviation | Ref ECL Shift |
|---|---|---|---|---|---|---|---|
| 243677184 | 147736 | 138264 | 93.59 | 127054 | 3 | 0.001 | 0.001 |

TSBA [Rev 3.90] Paracoccus . . . . . . . . . . . . . . . . 0.335
P. denitrificans . . . . . . . . . . . . . . . . . 0.335
Bradyrhizobium . . . . . . . . . . . . . . . . . 0.313 (4D, Rhiz X medium)
B. japonicum . . . . . . . . . . . . . . . . . . 0.313 (4D, Rhiz X medium)
B. j. GC subgroup A . . . . . . . . . . . . . . . 0.313 (4D, Rhiz X medium)
Methylobacterium . . . . . . . . . . . . . . . . 0.295 (48h, Pseudomonas mesophilica)
M. mesophilicum* . . . . . . . . . . . . . . . . 0.295 (48h, Pseudomonas mesophilica)
M. radiotolerans . . . . . . . . . . . . . . . . 0.244 (48h, Pseudomonas radiora)
M. extensum . . . . . . . . . . . . . . . . . 0.186 (48h)
CLIN [Rev 3.90] Ochrobactrum . . . . . . . . . . . . . . . . 0.233
O. anthropi* . . . . . . . . . . . . . . . . . . 0.233
Sphingomonas . . . . . . . . . . . . . . . . . 0.168 (Pseudomonas paucimobilis)
S. paucimobilis . . . . . . . . . . . . . . . . 0.168 (Pseudomonas paucimobilis)

Fig. 5

| RT | Area | Ar/Ht | Respon | ECL | Name | % | Comment 1 | Comment 2 |
|---|---|---|---|---|---|---|---|---|
| 1.665 | 239780224 | 0.032 | . . . | 7.033 | SOLVENT PEAK . . . . | . . . | < min rt | |
| 2.347 | 544 | 0.028 | . . . | 7.566 | . . . . . . . . . . . | . . . | < min rt | |
| 2.094 | 560 | 0.027 | . . . | 7.844 | . . . . . . . . . . . | . . . | < min rt | |
| 4.369 | 16792 | 0.034 | 1.695 | 11.420 | 10:0 3OH . . . . . . | 4.14 | ECL deviates -0.003 | |
| 4.870 | 3080 | 0.041 | . . . | 11.943 | . . . . . . . . . . . | . . . | | |
| 4.925 | 6464 | 0.038 | 1.071 | 12.000 | 12:0 . . . . . . . . | 1.56 | ECL deviates -0.000 | Reference 0.000 |
| 5.235 | 1624 | 0.053 | . . . | 12.259 | . . . . . . . . . . . | . . . | | |
| 6.370 | 23030 | 0.041 | 1.026 | 13.176 | 12:0 2OH . . . . . . | 5.34 | ECL deviates -0.002 | |
| 6.764 | 15360 | 0.041 | 1.016 | 13.455 | 12:0 3OH . . . . . . | 3.52 | ECL deviates -0.000 | |
| 7.535 | 3636 | 0.043 | 0.998 | 14.000 | 14:0 . . . . . . . . | 0.82 | ECL deviates 0.000 | Reference 0.000 |
| 10.509 | 109552 | 0.048 | 0.950 | 15.819 | Sum In Feature 4 . . | 23.46 | ECL deviates 0.002 | 16:1 w7c/15 iso 2OH |
| 10.827 | 102120 | 0.048 | 0.946 | 16.001 | 16:0 . . . . . . . . | 21.78 | ECL deviates 0.001 | Reference 0.001 |
| 11.045 | 10608 | 0.053 | 0.943 | 16.130 | 15:0 ISO 3OH . . . . | 2.26 | ECL deviates -0.005 | |
| 11.330 | 10112 | 0.049 | . . . | 16.292 | . . . . . . . . . . . | . . . | | |
| 12.375 | 6256 | 0.052 | 0.929 | 16.888 | 17:0 CYCLO . . . . . | 1.31 | ECL deviates -0.000 | Reference -0.000 |
| 14.045 | 169864 | 0.051 | 0.916 | 17.825 | Sum In Feature 7 . . | 35.07 | ECL deviates 0.000 | 18:1 w9c/w12t/w7c |
| 14.355 | 1488 | 0.054 | 0.914 | 17.999 | 18:0 . . . . . . . . | 0.31 | ECL deviates -0.001 | Reference 0.000 |
| 14.603 | 16104 | 0.057 | . . . | 18.139 | . . . . . . . . . . . | . . . | | |
| 15.951 | 2192 | 0.061 | 0.906 | 18.901 | 19:0 CYCLO w8c . . . | 0.45 | ECL deviates 0.001 | Reference 0.002 |
| ----- | 109552 | . . . | . . . | . . . | SUMMED FEATURE 4 . . | 23.46 | 16:1 w7c/15 iso 2OH | 15:0 ISO 2OH/16:1w7c |
| ----- | 169864 | . . . | . . . | . . . | SUMMED FEATURE 7 . . | 35.07 | 18:1 w7c/w9t/w12t | 18:1 w9c/w12t/w7c |
| ----- | . . . . . | . . . | . . . | . . . | . . . . . . . . . . . | . . . | 18:1 w12t/w9t/w7c | |

| Solvent Ar | Total Area | Named Area | % Named | Total Amnt | Nbr Ref | ECL Deviation | Ref ECL Shift |
|---|---|---|---|---|---|---|---|
| 39780224 | 497152 | 467432 | 93.98 | 443648 | 6 | 0.002 | 0.001 |

```
TSBA [Rev 3.90] Pseudomonas . . . . . . . . . . . . . . . . . 0.457
                P. aeruginosa . . . . . . . . . . . . . . . . 0.457
CLIN [Rev 3.90] Pseudomonas . . . . . . . . . . . . . . . . . 0.326
                P. aeruginosa* . . . . . . . . . . . . . . . 0.326
                P. stutzeri . . . . . . . . . . . . . . . . . 0.147
                P. putida . . . . . . . . . . . . . . . . . . 0.115
                   P. p. biotype A* . . . . . . . . . . . . . 0.115
                Chryseomonas . . . . . . . . . . . . . . . . 0.153  ("Pseudomonas VE1")
                C. luteola . . . . . . . . . . . . . . . . . 0.153  ("Pseudomonas VE1")
```

Fig. 6

| RT | Area | Ar/Ht Respon | ECL | Name | % | Comment 1 | Comment 2 |
|---|---|---|---|---|---|---|---|
| 1.660 | 248210304 | 0.031 | 7.034 | SOLVENT PEAK | . | < min rt | |
| 1.857 | 920 | 0.025 | 7.407 | . | . | < min rt | |
| 1.929 | 1296 | 0.029 | 7.562 | . | . | < min rt | |
| 9.919 | 1216 | 0.049 | 0.957 | 15.486 | Sum In Feature 3 | 4.89 | ECL deviates 0.004 | 16:1 ISO I/14:0 3OH |
| 10.480 | 3256 | 0.040 | 0.950 | 15.816 | Sum In Feature 4 | 13.00 | ECL deviates -0.001 | 16:1 w7c/15 iso 2OH |
| 10.789 | 1712 | 0.051 | 0.947 | 15.999 | 16:0 | 6.81 | ECL deviates -0.001 | Reference -0.003 |
| 13.469 | 1120 | 0.058 | 0.924 | 17.517 | 16:0 3OH | 4.35 | ECL deviates -0.003 | |
| 14.009 | 16984 | 0.050 | 0.920 | 17.021 | Sum In Feature 7 | 65.69 | ECL deviates -0.001 | 18:1 w7c/w9t/w12t |
| 16.249 | 1376 | 0.065 | 0.910 | 19.069 | 18:1 2OH | 5.26 | ECL deviates 0.001 | |
| ******* | 1216 | | | SUMMED FEATURE 3 | 4.89 | 12:0 ALDE ? | unknown 10.928 |
| ******* | | | | | | 16:1 ISO I/14:0 3OH | 14:0 3OH/16:1 ISO I |
| ******* | 3256 | | | SUMMED FEATURE 4 | 13.00 | 16:1 w7c/15 iso 2OH | 15:0 ISO 2OH/16:1w7c |
| ******* | 16984 | | | SUMMED FEATURE 7 | 65.69 | 18:1 w7c/w9t/w12t | 18:1 w9c/w12t/w7c |
| ******* | | | | | | 18:1 w12t/w9t/w7c | |

| Solvent Ar | Total Area | Named Area | % Named | Total Amnt | Nbr Ref | Ref ECL Deviation | Ref ECL Shift |
|---|---|---|---|---|---|---|---|
| 248210304 | 25664 | 25664 | 100.00 | 23797 | 1 | 0.002 | 0.003 |

QUESTION ANALYSIS: TOTAL AREA LESS THAN 50000. CONCENTRATE AND RE-RUN.

TSBA [Rev 3.90] Azospirillum . . . . . . . . . . . . . . . 0.786
A. brasilense . . . . . . . . . . . . . . . 0.786
CLIN [Rev 3.90] Roseomonas . . . . . . . . . . . . . . . 0.599
R. fauriae** . . . . . . . . . . . . . . . 0.590

Fig. 7

| RT | Area | Ar/Ht Respon | ECL | Name | % | Comment 1 | Comment 2 |
|---|---|---|---|---|---|---|---|
| 1.664 | 241080192 | 0.032 | 7.031 | SOLVENT PEAK | | < min rt | |
| 10.814 | 8176 | 0.048 | 16.000 | 16:0 | 6.88 | ECL deviates 0.000 | Reference -0.001 |
| 14.041 | 102160 | 0.052 | 17.824 | Sum In Feature 7 | 83.22 | ECL deviates -0.001 | 18:1 w9c/w12t/w7c |
| 14.352 | 2552 | 0.054 | 17.999 | 18:0 | 2.07 | ECL deviates -0.001 | Reference -0.002 |
| 14.608 | 1544 | 0.077 | 18.143 | | | | |
| 15.949 | 9720 | 0.053 | 18.901 | 19:0 CYCLO w8c | 7.83 | ECL deviates 0.001 | Reference 0.001 |
| ----- | 102160 | | | SUMMED FEATURE 7 | 83.22 | 18:1 w7c/w9t/w12t | 18:1 w9c/w12t/w7c |
| ***** | | | | | | 18:1 w12t/w9t/w7c | |

| Solvent Ar | Total Area | Named Area | % Named | Total Amnt | Nbr Ref | ECL Deviation | Ref ECL Shift |
|---|---|---|---|---|---|---|---|
| 241080192 | 124152 | 122608 | 98.76 | 112432 | 3 | 0.001 | 0.001 |

| | | |
|---|---|---|
| TSBA [Rev 3.90] Ochrobactrum | · · · · · · · · · · · | 0.620 (Achromobacter Vd, CDC group Vd) |
| O. anthropi | · · · · · · · · · · · | 0.620 (Achromobacter Vd, CDC group Vd) |
| Bradyrhizobium | · · · · · · · · · · · | 0.587 (4D, Rhiz X medium) |
| B. japonicum | · · · · · · · · · · · | 0.587 (4D, Rhiz X medium) |
| B. f. GD subgroup A | · · · · · · · · · · · | 0.587 (4D, Rhiz X medium) |
| Xanthobacter | · · · · · · · · · · · | 0.500 |
| X. agilis | · · · · · · · · · · · | 0.500 |
| X. flavus | · · · · · · · · · · · | 0.254 |
| CLIN [Rev 3.90] Ochrobactrum | · · · · · · · · · · · | 0.548 |
| O. anthropi* | · · · · · · · · · · · | 0.548 |

Fig. 8

| RT | Area | Ar/Ht | Respon | ECL | Name | % | Comment 1 | Comment 2 |
|---|---|---|---|---|---|---|---|---|
| 1.664 | 248735360 | 0.031 | . . . | 7.031 | SOLVENT PEAK . . . . . . . . . | | < min rt | |
| 1.770 | 6064 | 0.024 | . . . | 7.231 | . . . . . . . . . . . . . . | | < min rt | |
| 1.862 | 2552 | 0.027 | . . . | 7.405 | . . . . . . . . . . . . . . | | < min rt | |
| 1.945 | 1096 | 0.034 | . . . | 7.562 | . . . . . . . . . . . . . . | | < min rt | |
| 10.815 | 2752 | 0.046 | 0.946 | 15.999 | 16:0 . . . . . . . . . | 2.81 | ECL deviates -0.001 | Reference -0.001 |
| 11.327 | 1448 | 0.054 | . . . | 16.291 | . . . . . . . . . . . . . . | . . . | - | . |
| 12.575 | 1712 | 0.058 | 0.927 | 17.002 | 17:0 . . . . . . . . . | 1.72 | ECL deviates 0.002 | Reference 0.001 |
| 13.500 | 968 | 0.059 | 0.920 | 17.521 | 16:0 3OH . . . . . . | 0.96 | ECL deviates 0.001 | |
| 14.041 | 90456 | 0.051 | 0.916 | 17.825 | Sum In Feature 7 . . | 89.56 | ECL deviates -0.000 | 18:1 w9c/w12t/w7c |
| 14.352 | 3920 | 0.049 | 0.914 | 17.999 | 18:0 . . . . . . . . . | 3.87 | ECL deviates -0.001 | Reference -0.002 |
| 14.499 | 760 | 0.044 | . . . | 18.082 | . . . . . . . . . . . . . . | . . . | | |
| 14.613 | 4955 | 0.055 | . . . | 18.147 | . . . . . . . . . . . . . . | . . . | | |
| 17.575 | 1096 | 0.057 | 0.902 | 19.834 | 20:1 w9t . . . . . . | 1.07 | ECL deviates 0.001 | |
| ***** | 90456 | . . . | . . . | . . . | SUMMED FEATURE 7 . . | 89.56 | 18:1 w7c/w9t/w12t | 18:1 w9c/w12t/w7c |
| ***** | . . . | . . . | . . . | . . . | . . . . . . . . . . . . . . | . . . | 18:1 w12t/w9t/w7c | |

| Solvent Ar | Total Area | Named Area | % Named | Total Amt | Nbr Ref | ECL Deviation | Ref ECL Shift |
|---|---|---|---|---|---|---|---|
| 248735360 | 152664 | 100904 | 66.10 | 92494 | 3 | 0.001 | 0.001 |

QUESTION ANALYSIS: PERCENT AREA NAMED IS LESS THAN 85. CHECK FOR CONTAMINATION.

```
TSBA [Rev 3.90] Methylobacterium . . . . . . . . . . . . . . . 0.782  (48h, Pseudomonas radiora)
                 M. radiotolerans . . . . . . . . . . . . . . . 0.782  (48h, Pseudomonas radiora)
                 M. mesophilicum* . . . . . . . . . . . . . . . 0.708  (48h, Pseudomonas mesophilica)
                 M. zatmanii . . . . . . . . . . . . . . . . . 0.674  (48h)
              Rhodobacter . . . . . . . . . . . . . . . . . . . 0.657
                 R. sphaeroides . . . . . . . . . . . . . . . . 0.657
                 R. capsulatus . . . . . . . . . . . . . . . . 0.454
              Xanthobacter . . . . . . . . . . . . . . . . . . 0.647
                 X. flavus . . . . . . . . . . . . . . . . . . 0.647
CLIN [Rev 3.90] Methylobacterium . . . . . . . . . . . . . . . 0.512
                 M. mesophilicum . . . . . . . . . . . . . . . 0.512
              Ochrobactrum . . . . . . . . . . . . . . . . . . 0.403
                 O. anthropi* . . . . . . . . . . . . . . . . . 0.403
```

METHOD OF PURIFYING WATER, SUITABLE BACTERIA FOR THE METHOD AND USE THEREOF

FIELD OF THE INVENTION

The invention relates to a method of purifying waste water biologically, and to bacteria and a mixed bacterial population suitable for the method and the use thereof. The invention further relates to a bioreactor comprising said bacteria or mixed population.

BACKGROUND OF THE INVENTION

Conventionally, water can be purified both by physical and chemical means, for example by sedimentation, filtration or flocculation (WO94/5866 and WO88/5334). In order to remove organic compounds and other compounds that are difficult to purify it is also preferable to use so-called biological purification wherein the water to be purified is brought into contact with microorganisms that decompose pollution agents. Biological water treatment methods are suited for use both in conventional water treatment plants and industrial waste water treatment plants. Biological water treatment has also been tested in systems where water is recycled (Fl 964141). Biological water treatment is also needed to purify seep water of a dump, for example, before the seep water is discharged into the environment.

The biological purifying method is, however, more difficult to control than the physical or chemical purifying methods. Firstly, microorganisms to decompose pollution agents must be found. Secondly, the microorganisms must be capable of easily surviving and reproducing under conditions during the water treatment process. In other words, the microorganisms used for purifying water must be competitive ones so as to prevent other organisms in the water from overruling. In addition, the microorganisms used for purifying water must not be sensitive to the changes in their environment that often occur during water treatment processes when the load varies.

Many kinds of microorganisms have been used for purifying water, including bacteria and protozoa, such as the ciliates. Bacteria that have often been used include species of the Pseudomonas genus, but also members of the Alcagenes, Acinetobacter or Rhodococcus genera are often used. Mixed populations, some identified and some unidentified, comprising a great number of different microorganisms are often used. Aerobic or facultative microorganisms are best suited to purifying water, in which case it is appropriate to pump air into the water to be purified so as to make the purification process more efficient.

When microorganisms are cultivated, the growth medium should normally be sterilized so as to prevent the cultivation from becoming contaminated by external organisms. Since large amounts of water are processed while purifying waste water, the amount of necessary biomass for the biological purification is also large. To produce such biomass under sterile conditions is both laborious and expensive; hence, it would be most desirable if the biomass could be produced under non-sterile conditions without any danger of becoming contaminated. The present invention now provides a novel fermentation technology with no need to sterilize. This is possible when microorganisms particularly suitable for the method are used and these microorganisms are fed on nutrients suitable for them.

SUMMARY OF THE INVENTION

The present invention relates to microorganisms that are surprisingly well suited to biological purification of waste water. These microorganisms meet particularly well the aforementioned requirements set for microorganisms suitable for the biological purification of water. In addition, the microorganisms of the invention are so specific that their biomass can be produced under non-sterile conditions by using a growth medium where other microorganisms are unable to compete. This enables large savings in the costs and energy consumption of a biological water purification process, the purification results also being excellent. Water purified according to the invention is even recyclable.

The invention thus relates to the bacteria Bacillus sp. DT-1 having the deposit number DSM 12560 and progeny thereof, Pseudomonas sp. DT-2, subsequently identified as *Pseudomonas azelaica* having the deposit number DSM 12561 and progeny thereof, and the former Pseudomonas sp. now being Rhizobium sp. and having the deposit number DSM 12562 and progeny thereof. Later 16S rDNA analyses have shown that this bacterium most closely resembles the members of the Rhizobium genus, so hereafter, it will be considered as one of them. The invention further relates to the following bacterial strains promoting water purification: *Pseudomonas azelaica* DT-6 having the deposit number DSM 13516, Azospirillium sp. DT-10 having the deposit number DSM 13517, *Ancylobacter aquaticus* DT-12 having the deposit number DSM 13518, and Xanthobacter sp. DT-13 having the deposit number DSM 13519, and progeny thereof. DSM 12560–12562 have been deposited at Deutsche Sammlung von Mikroorganismen und Zelikulturen GmbH on 1 Dec. 1998, and DSM 13516–13519 on 29 May 2000.

The invention further relates to a bacterial mixed population characterized by comprising the bacterium Bacillus sp. DT-1 having the deposit number DSM 12560, *Pseudomonas azelaica* DT-2 having the deposit number DSM 12561, and/or Rhizobium sp. DT-5 having the deposit number DSM 12562, and progeny thereof.

The invention further relates to the use of the aforementioned bacteria or bacterial mixed populations in waste water treatment and to a method of purifying waste water, characterized by purifying water biologically by microorganisms belonging to the group Bacillus sp. DT-1 having the deposit number DSM 12560, *Pseudomonas azelaica* DT-2 having the deposit number DSM 12561, and Rhizobium sp. DT-5 having the deposit number DSM 12562, and progeny thereof.

The invention further relates to a bioreactor characterized by comprising microorganisms belonging to the group Bacillus sp. DT-1 having the deposit number DSM 12560, *Pseudomonas azelaica* DT-2 having the deposit number DSM 12561, and Rhizobium sp. DT-5 having the deposit number DSM 12562, and progeny thereof. A bioreactor is a reactor in which a biological purification process is conducted.

DRAWINGS

FIG. 1 schematically shows a purification system for seep water,

FIG. 2b is a print of a fatty acid analysis of bacterial strain DT-1,

FIG. 3b is a print of a fatty acid analysis of bacterial strain DT-2,

FIG. 4 is a print of a fatty acid analysis of bacterial strain DT-5,

FIG. 5 is a print of a fatty acid analysis of bacterial strain DT-6,

FIG. 6 is a print of a fatty acid analysis of bacterial strain DT-10,

FIG. 7 is a print of a fatty acid analysis of bacterial strain DT-12, and

FIG. 8 is a print of a fatty acid analysis of bacterial strain DT-13.

DETAILED DESCRIPTION OF THE INVENTION

Figure 1:
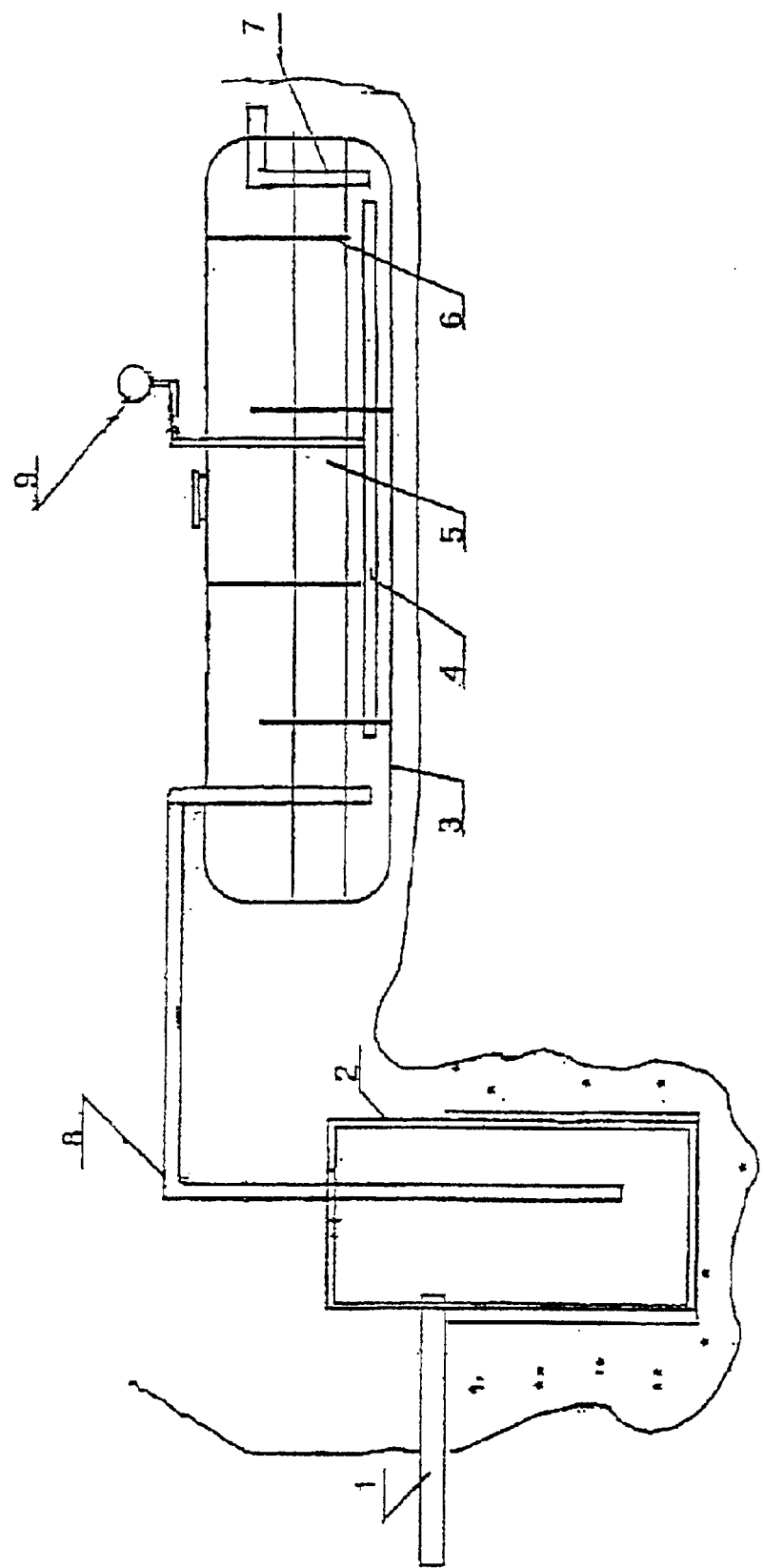

Microorganisms growing in a soap mixture were enriched from waste water of an industrial plant and then adapted by cultivating them in a bioreactor comprising waste water from a dump. Three bacterial strains were thus isolated that were superior to the others. Said bacterial strains are Bacillus sp. DT-1 having the deposit number DSM 12560, Pseudomonas azelaica DT-2 having the deposit number DSM 12561 and Rhizobium sp. DT-5 having the deposit number DSM 12562. These bacteria can be cultivated in tap water comprising about 1–4 g/l of soap. Extremely few microorganisms can actively grow under such conditions; therefore, this growth medium needs not be sterilized when biomass of said three bacteria is being produced. The strains tolerate as high amounts of soap as about 40 g/l. They grow best in a soap content of about 0.3–0.5 g/l.

In addition to being capable of growing in a growth medium where most other bacteria are incapable of reproducing, said bacterial strains are extremely efficient in removing the organic load of waste water. This is usually measured as total COD, which means the total chemical oxygen consumption (mg $O_2$/l). The isolated bacterial strains can particularly decompose compounds that do not decompose easily, such as chlorophenoles, polycyclic aromatic hydrocarbons (PAH compounds) and oils. They also remove heavy metals. The scope of the invention also encompasses progeny of said strains, referring to progeny of said strains that have substantially the same waste water treatment capacity as the deposited strains.

The bacteria Bacillus sp. DT-1, Pseudomonas azelaica DT-2 and Rhizobium sp. DT-5 further tend to flocculate, in which case they form a so-called bionetwork, which comprises lumps comprising microorganisms and other particles and which promotes the purification.

Particularly good waste water treatment results are achieved when biological water purification utilizes a bacterial mixed population comprising one or more bacteria selected from a group comprising the bacteria Bacillus sp. DT-1, Pseudomonas azelaica DT-2 and Rhizobium sp. DT-5, and progeny thereof. The best purification results are achieved when a mixed population is used which comprises all three bacterial strains and/or progeny thereof. In addition to these three strains, the bacterial mixed population may further comprise other microorganism strains that are useful in water treatment and that have a favourable combined effect on the purification capacity.

The best purification results are achieved when the microorganism strains DT-1, DT-2, and/or DT-5 are used together with one or more bacterial strains from the group Pseudomonas azelaica DT-6 having the deposit number DSM 13516, Azospirillium sp. DT-10 having the deposit number DSM 13517, Ancylobacter aquaticus DT-12 having the deposit number DSM 13518, and Xanthobacter sp. DT-13 having the deposit number DSM 13519, and progeny thereof. Said four strains were isolated from the biofilm of the last unit of a four cascade bioreactor for treating water containing a mixture of soaps. They can be grown in the same growth medium and under the same conditions as DT-1, DT-2 and DT-5, DT-6, DT-10, DT-12 and DT-13 improve the immobilization properties of the biofilm to supporting matrices when they are mixed with strains DT-1, DT-2 and DT-5. Association of the strains also improves the treatment process of waste water as a result of more tolerance of the biofilm formed against poisonous substances.

Bacillus sp. DT-1 is a rod which is about 1.0–1.2 μm in width and 3.0–6.0 μm in length. Partial sequencing of the 16S rDNA shows a similarity of 99.3% to B. cereus and 100% to B. thuringiensis. In identification tests DT-1 reacted as indicated below:

| | |
|---|---|
| Anaerobic growth | + |
| VP reaction | + |
| pH in VP broth | 4.8 |
| Growth in medium pH 5.7 | + |
| 2% NaCl | + |
| 5% | + |
| 7% | − |
| 10% | − |
| Lysozyme broth | + |
| Acid from | |
| L-arabinose | − |
| D-xylose | − |
| D-mannitol | − |
| D-fructose | + |
| Lecithinase | + |
| Hydrolysis of: | |
| casein | + |
| Tween 80 | weak |
| aesculin | + |
| Use of propionate | − |
| Indol reaction | − |
| Phenylalanine deaminase | + |
| Hemolysis | + |
| Growth in penicillin 900 U/ml | + |

Pseudomonas azelaica DT-2 is a rod which is 0.5–0.7 μm in width and 1.5–3.0 μm in length with 1–3 polar flagella and lacking fluorescent pigments. The partial sequencing of the 16S rDNA is 99.8% similar to Ps. azelaica. It reacts as follows:

| | |
|---|---|
| Lysis by 30% KOH | + |
| Aminopeptidase (Cerny) | + |
| Lecithinase | − |
| Utilization of | |
| arabinose | − |
| adipat | + |
| mannitol | − |
| gluconat | + |
| caprat | + |

Rhizobium sp. DT-5 is a rod which is 0.5–0.7 μm in width and 1.5–3.0 μm in length. Partial 16S rDNA sequencing shows a 98.6% similarity to R. giardinii and 98.6% similarity to Phyllobacterium myrisinacearum. Physiological test results are given below. They do not confirm any of these genera.

Other morphological, physiological and biochemical characteristics of bacterial strains DT-1, DT-2 and DT-5 are shown in Table 1.

TABLE 1

Morphological, physiological and biochemical characteristics of the bacterial strains.

| Characteristic | Strain reaction | | |
|---|---|---|---|
| | DT-1 | DT-2 | DT-5 |
| Cell morphology | Straight or slightly curved rod | Straight rod | Rod |
| Motility | + | + | + |
| Formation of endospores | + | − | − |
| Spore form | E | − | − |
| Spore position | T | − | − |
| Expanded sporangium | − | − | − |
| Gram's stain | P | N | N |
| Catalase | + | + | + |
| Oxidase | + | + | + |
| Reduction of nitrate to nitrite | + | + | − |
| Denitrification | − | + | − |
| Argininedihydrolase | + | + | − |
| Hydrolysis: | | | |
| starch | + | − | − |
| gelatin | + | − | − |
| acetamide | − | − | + |
| Urease | − | − | + |
| Splitting up aromatic ring | − | Orto | − |
| Growth at temperature of: | | | |
| 35° C. | + | + | + |
| 39° C. | + | + | − |
| 40° C. | + | − | − |
| 41° C. | + | − | − |
| 43° C. | − | − | − |
| Utilization of: | | | |
| Acetate | + | + | + |
| D-Alanine | − | + | − |
| L-Alanine | − | + | + |
| β-Alanine | − | + | − |
| L-Arginine | + | + | + |
| L-Asparagine | ± | + | ± |
| L-Aspartate | ± | + | − |
| Citrate | + | + | − |
| L-Cystein | − | − | + |
| L-Cystin | − | − | − |
| Ethanol | − | + | − |
| D-glucose | + | + | + |
| Glutamate | + | + | ± |
| Glycerol | + | − | − |
| Glycine | − | − | − |
| L-Histidine | − | + | + |
| p-Hydroxybenzoate | − | + | − |
| meso-inositol | − | − | + |
| Lactose | − | − | − |
| L-Leucine | ± | + | + |
| L-Lysine | ± | + | − |
| Lysis by 3% KOH | + | | |
| Aminopeptidase (Cerny) | + | | |
| Anaerobic growth | − | | |
| Simmons citrate | + | | |
| Utilization of | | | |
| arabinose | + | | |
| mannose | + | | |
| mannitol | + | | |
| adipat | − | | |
| Malat | + | + | − |
| Malonate | + | − | − |
| Methanol | − | − | − |
| L-Methionine | − | − | − |
| L-Proline | − | + | + |
| DL-Serine | + | − | − |
| Succinate | + | + | + |
| Saccharose | ± | − | + |
| DL-Threonine | − | − | − |
| D-Trehalose | + | − | + |
| DL-Tryptophan | ± | − | − |
| L-Tyrosine | − | + | ± |

P = positive
N = negative
E = of elliptical shape
T = terminal

Figure 2A:
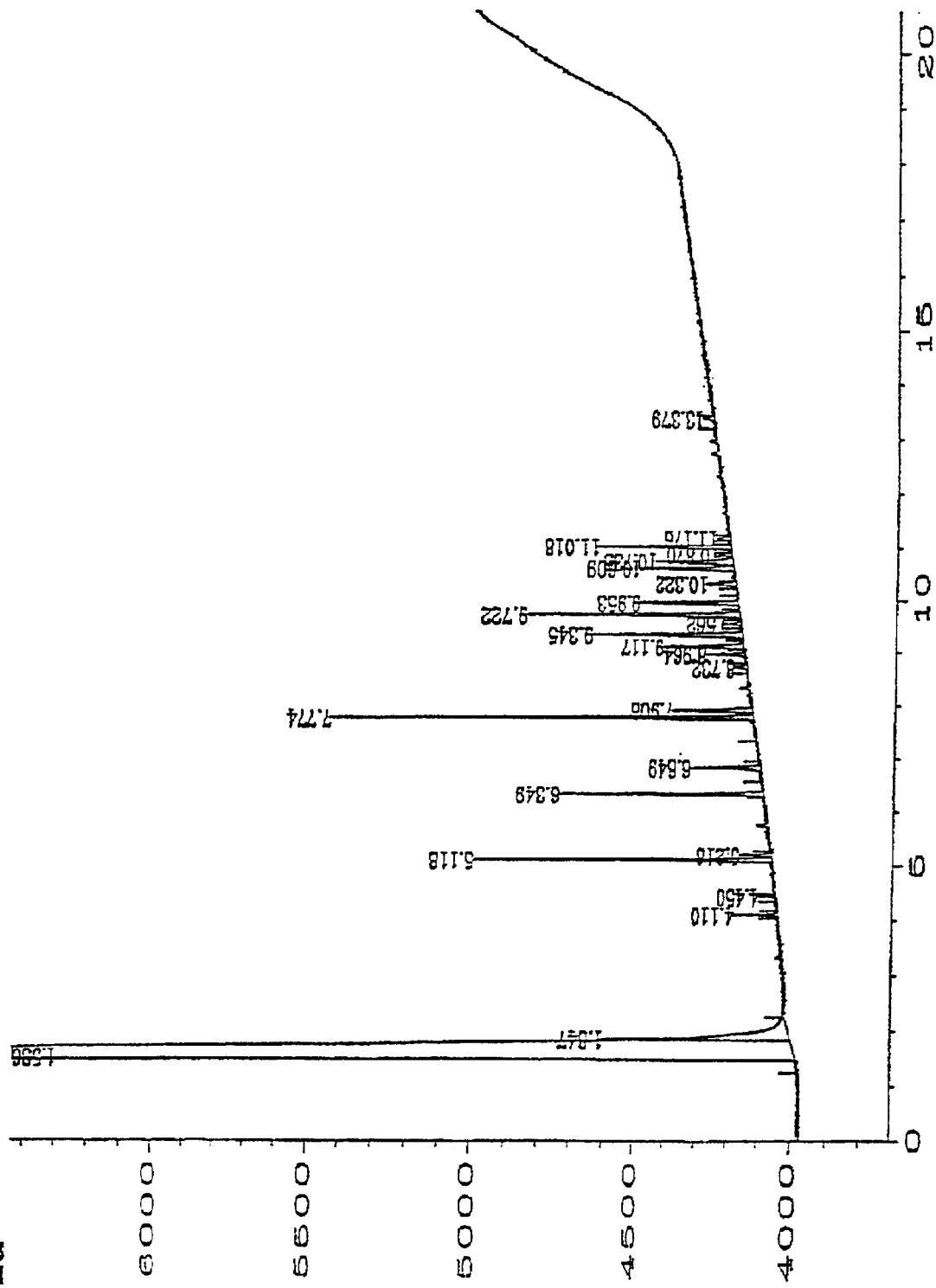
FIG. 2a shows a profile of the fatty acids of bacterial strain DT-1.
Figure 3A:
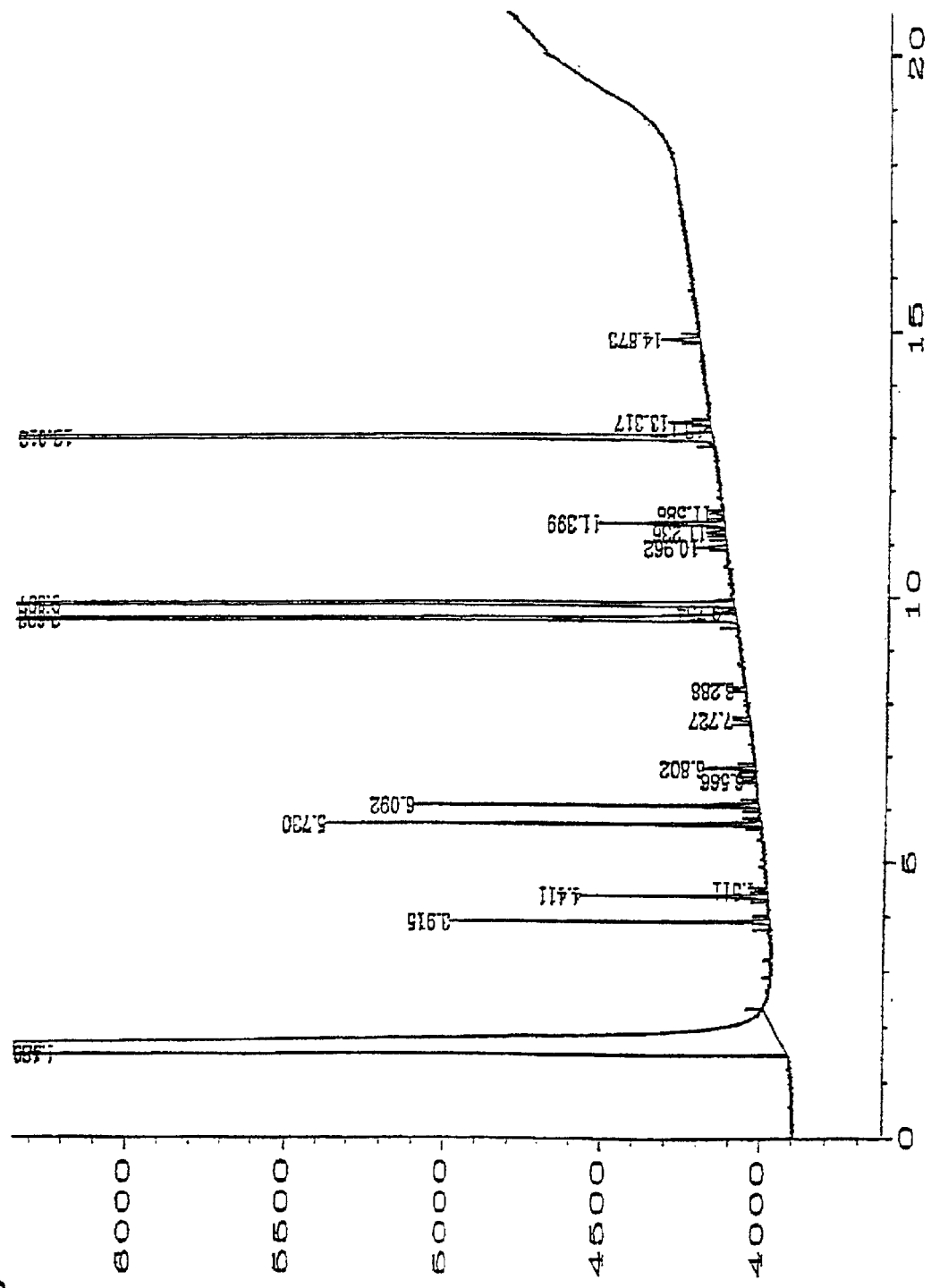
FIG. 3a shows a profile of the fatty acids of bacterial strain DT-2.

Furthermore, the profiles of the fatty acids of bacterial strains DT-1, DT-2 and DT-5 were determined and they are shown in FIGS. 2 to 4. The bacteria were grown 24 hours at 28° C. on tryptic soy broth agar and methyl esters were prepared for the fatty acid analysis of the whole cell, as described in publication Structure and composition of biological slimes on paper and board machines. Appl. Environ, Microbiol. 60:641–653 by Väisänen, O. M., E-L. Nurmiaho-Lassila, S. A. Marmo and M. S. Salkinoja-Salonen (1994). An aerobic TSBA library, version 3.9 (MIDI Inc., Newark, Del., USA), was used. The retention time (in minutes) is shown on the x-axis of FIGS. 2a and 3a, and the intensity of a peak is shown on the y-axis of the same figures. The corresponding prints of the fatty acid analyses are shown in FIGS. 2b, 3b and 4. The profile of the fatty acids of DT-1 is typical of the B. cereus group. The profile of DT-2 is typical of the RNA group I of the pseudomonads, and the profile of DT-5 points to the Rhizobium group.

Pseudomonas azelaica DT-6 is a 0.5–0.7 μm wide and 1.5–3.0 μm long gram-negative motile rod having 1–3 polar flagella and lacking fluorescent pigments. Its fatty acid analysis print (FIG. 5) is typical of the RNA group I of the pseudomonads. The partial sequencing of the 16S rDNA shows a 99.8% similarity to Ps. azelaica. DT-6 has the following physiological reactions:

| | |
|---|---|
| Lysis by 3% KOH | + |
| Aminopeptidase (Cerny) | + |
| Oxidase | + |
| Catalase | + |
| ADH | + |
| NO$_2$ from NO$_3$ | + |
| Denitrification | weak |
| Urease | − |
| Hydrolysis of gelatin | − |
| Lecithinase | − |
| Utilization of (AP1 2ONE) | |
| glucose | + |
| arabinose | − |
| adipat | + |
| malat | + |
| mannitol | − |

-continued

| | |
|---|---|
| gluconat | + |
| caprat | + |

Azospirillium sp. DT-10 is a 0.8–1.2 μm wide and 2.0–4.0 μm long gram-negative rod. Its fatty acid analysis print (FIG. 6) is typical of the α-subgroup of the proteobacteria and points to the genus Azospirillium. The partial sequencing of the 16S rDNA shows similarities between 92% and 97.4% to different members of the genus Azospirillium. The highest similarity 97.4% was found to *Azospirillium lipoferum*. The physiological reactions of DT-10 are shown below. They point to the genus Azospirillium but are not typical of *A. lipoferum*. DT-10 is possibly a new species of this genus.

| | |
|---|---|
| Lysis by 3% KOH | weak |
| Aminopeptidase (Cerny) | + |
| Oxidase | + |
| Catalase | + |
| NO$_2$ from NO$_3$ | + |
| Urease | + |
| ADH | – |
| Hydrolysis of | |
| gelatin | – |
| esculin | – |
| Utilization of (sole carbon source) | |
| glucose | – |
| arabinose | – |
| adipat | – |
| malat | + |
| mannitol | – |
| phelyacetat | – |
| citrate | – |
| caprat | – |
| gluconat | – |
| maltose | – |
| n-acetylglucosamin | – |
| α-ketoglutarate | + |
| sucrose | – |
| m-inositol | – |
| D-fructose | + |
| rhamnose | – |
| arabitol | – |
| ribose | – |
| Growth at 41° C. | – |
| with 3% NaCl | – |

*Ancylobacter aquaticus* DT-12 is a gram-negative curved rod which is 0.5–0.7 μm in width and 1.5–2.0 μm in length. The partial sequence of the 16S rDNA shows a similarity of 98.8% to *Ancylobacter aquaticus*. *Thiobacillus novellus* shows a similarity of 97.8%. The fatty acids (FIG. 7) point to the α-proteobacteria. The physiological tests as shown below clearly identify the species *Ancylobacter aquaticus*.

| | |
|---|---|
| Lysis by 3% KOH | weak |
| Aminopeptidase (Cerny) | + |
| Oxidase | + |
| Catalase | + |
| ADH | – |
| Urease | – |
| Hydroiysis of gelatin | – |
| esculin | + |
| NO$_2$ from NO$_3$ | – |
| Denitrification (24 h) | – |

-continued

| | |
|---|---|
| Utilization of | |
| glucose | + (weak) |
| citrate | + |
| arabinose | + |
| mannose | – |
| mannitol | + |
| maltose | – |
| N-acetylglucosmin | – |
| gluconat | – |
| malat | + |
| phenylacetat | – |
| methanol | + |
| formiate | weak |

Xanthobacter sp. DT-13 is an irregular, motile, gram-negative rod which is 0.8–1.0 μm in width and 1.5–3.0 μm in length. The partial sequences of the 16S rDNA show similarities of 98.5% to 99.3% to different members of the genus Xanthobacter. *X. falvus* shows the highest similarity (99.3%). The profile of the fatty acids is typical of the subclass of α-proteobacteria. The physiological tests are not able to distinguish reliably between the species of this genus (i.e. no pigment production detected, no slime production, etc.). The physiological data are given below:

| | |
|---|---|
| Lysis by 3% KOH | + |
| Aminopeptidase (Cerny) | + |
| Oxidase | + |
| Catalase | + |
| ADH | – |
| Urease (24 h) | – |
| Hydrolysis of gelatin | – |
| esculine | – |
| NO$_3$ utilization | – |
| Utilization of | |
| phenylacetate | – |
| citrate | – |
| malate | + |
| ambinose | – |
| mannose | – |
| mannit | – |
| caprat | – |
| maltose | – |
| adipate | + |
| malonate | + |
| methanol | – |
| m-inosit | – |
| m-tartrate | + |
| D-gluconate | + |
| phelylalanine | – |

The above-described bacteria are suited for use in purifying waste water. The bacteria can then be first grown in a minimal salt medium (KSN) in a shaker. Soy pepton (0.5 g/l), trypton (0.1 g/l), glucose (0.2 g/l) and potassium acetate (0.3 g/l) may be added, if desired. The growing temperature of the bacteria is about 20–30° C. After this, the volume of the culture is then increased in order to produce the necessary biomass for purifying the water. This stage no longer needs to be conducted under sterile conditions, in which case tap water wherein about 0.5–4 g/l of soap has been added can be used as the growth medium. The soap used is preferably a mixture containing anionic, cationic, amphoteric and non-ionic tensides. It is preferable to use a mixture of different soaps, such as cleaning agents, fabric conditioners and detergents for clothes and dishes. The bacteria are grown as a submerged culture with air pumped thereto. The biomass can be produced as a batch culture, but preferably, it is produced as a continuous culture, or chemostat culture. It is preferable to use a carrier in the production of the biomass. Any common carrier, for example a plastic one, is suitable for this purpose. The produced biomass is then transferred into a water treatment reactor, into which the water to be purified is conveyed. A carrier for the bacteria is also used in the reactor, the carrier preferably being the same as used in the production of the biomass. The carrier is preferably one having a specific density lower than 1 g/cm$^3$. The carrier is generally held in place in a tank by means of a net ('fixed carrier'), for example, but sometimes the carrier is allowed to float freely in the tank ('swimming carrier').

The method of the invention is suited particularly to purifying seep water of a dump, which is here described in closer detail with reference to FIG. 1. A dump is usually surrounded by a ditch to collect the seep water. Seep water refers to water seeping from a dump due to rain and ground water. This seep water containing both surface water and cavity water is usually first conveyed to a tank wherefrom the water is conveyed through a purification process before being discharged into the environment. The seep water obtained both from deep and shallow ground is preferably first conveyed to a settlement basin, from which the water is filtered through an inlet pipe 1 to a filtrate well 2, and from there, through a transfer pipe 8 to a bioreactor 3 containing said bacteria and a carrier 5. The bacteria form a so-called biofilm around the carrier. The carrier with its bacteria is usually kept below the surface of the water by means of a net. The bioreactor preferably comprises one or more separating walls 6 arranged to force the water to circulate in the reactor. The separating walls may be arranged on opposite walls, for example, as shown in FIG. 1. The reactor usually further comprises an aerator 9 for conveying air into the reactor through an aeration pipe 4. The bioreactor further comprises an outlet pipe 7, through which processed water is discharged from the reactor.

In addition to purifying seep water, the present invention is extremely well suited also to purifying household and industrial grey water. Grey water refers to waste water other than that originating from lavatories, e.g. water from showers, handbasins, bath tubs and laundry rooms. The purification method of the invention is also suited to purifying waste water from lavatories, which is called black water. The method of the invention can also be used to purify laundry and industrial waste water, which often contains a large amount of organic waste, such as oil, polycyclic aromatic hydrocarbons (PAH compounds) and/or heavy metals. The method is also suitable for purifying waste water originating from food industry and water in swimming pools.

EXAMPLE 1

Production of Biomass and Start of a Bioreactor

Bacillus sp. DT-1, *Pseudomonas azelaica* DT-2 and Rhizobium sp. DT-5 were each transferred to 200 ml of sterilized minimum salt medium (KSN) of the following composition (g/l of distilled water): $K_2HPO_4 \times 3H_2O$—1.0, $NaH_2PO_4 \times 2H_2O$—0.25, $(NH_4)_2SO_4$—0.1, $MgSO_4 \times 7H_2O$—0.04, $Ca(NO_3)_2 \times 4H_2O$—0.01, yeast extract—0.05, pH 7.0–7.3, and soap mixture about 1 g/l. The soap mixture contained about equal amounts of the following detergents: laundry soap, Comfort, Cleani Family-fabric conditioner, Cleani Color, Serto Ultra, Bio Luvil, Ariel Futur, Omo Color, Tend Color, Tend Mega, Tend Total and Eko Kompakt (about 1 g/l in total). The bacteria were grown in a shaker (150–200 rpm), at 28° C.

When the growth was dense, all three cultures were brought to one 500-liter fermenter in order to produce the necessary biomass. The fermenter contained unsterilized tap water and a total of 4 g/l of the aforementioned soap mixture, and a plastic carrier containing polyethene and having a specific density of about 0.8 g/cm$^3$. The carrier was kept below the surface of the liquid by means of a net. The cultivation now continued under non-sterile conditions to a turbidity of about 2 (600 nm), and then as a chemostat culture. A first inoculum obtained from the fermenter was then introduced into a bioreactor (6 m$^3$) according to FIG. 1, diluted 1:10. The bioreactor contained seep water from a municipal dump which was first collected into a tank, wherefrom it was then transferred to a settlement basin for removal of solid matter and next, to a filtrate well, wherefrom it was pumped to the bioreactor. In principle, the system works by gravity, the only necessary pump being a submersible pump in the filtrate well. The bioreactor contained the same carrier as the fermenter used for producing the biomass. The carrier was kept below the liquid level by means of a net. The bacteria flocculated at the end of the bioreactor. The purification process was continuous, operating at a capacity of about 100 m$^3$/24 hours. Air was pumped so as to keep the oxygen content of the water to be processed >7 mg/l.

EXAMPLE 2

Purification of Seep Water

A bioreactor arranged according to Example 1 was used for purification of seep water from a municipal dump. The average COD of the waste water to be purified was about 800 mg—6 g $O_2$/l. The waste water contained chlorophenoles, PAH compounds and oil, for example. The removal of these substances from the waste water was monitored. According to Nordtest's technical report no. 329 (accepted 9603), the compounds were defined by a gas chromatograph equipped with a mass-selective detector. The results are shown in Table 2.

TABLE 2

| Detection | Before bioreactor | After bioreactor |
| --- | --- | --- |
| COD | 0.8–6 g/l | 100–200 mg/l |
| chlorophenoles | >1 mg/l | <1 µg/l |
| PAH | 1 mg/l | <1 µg/l |
| oil | 0.2–1 mg/l | 200 µg/l |

EXAMPLE 3

Purification of Municipal Waste Water (Full Scale)

Waste water from a municipal waste water plant was purified both in a manner conventionally used in the plant and by the method of the invention. Conventionally, waste water was purified by first conveying the waste water into a preliminary settlement basin in order to precipitate the solids onto the bottom. The preliminary settled water was then conveyed to an aerobic treatment basin, whereto ferrous sulphate for precipitating phosphate, and polyamine for precipitating biosludge were added. Herefrom, the water was further conveyed to a secondary settlement basin. The purification system of the invention comprised five tanks whose total volume was 7.5 m$^3$, the tanks being interconnected in the following order two anaerobic tanks, whereto bacteria DT-1, DT-2 and DT-5 were added without a carrier, one aerobic tank whereto a carrier was attached (by means of a net) on which the bacteria DT-1, DT-2 and DT-5 were immobilized, and two sedimentation tanks. The temperature was 8–15° C. The flow rate was 7.5 m³/24 hours of waste water. The aeration was conducted by recycling the water through the carrier. The results are shown in Table 3.

TABLE 3

| Parameter | Before treatment | After conventional purification | After purification of the invention |
|---|---|---|---|
| BOD7 mg $O_2$/l | 200–300 | 10–15 | 10–15 |
| $COD_{Cr}$ mg $O_2$/l | 250–500 | 60–75 | 40–50 |
| Total nitrogen mg N/l | 35–55 | 15–25 | 15–25 |
| Total phosphor mg P/l | 5–10 | 0.6–1.8 | 0.5–1.8 |
| Fec. stroptococci cfu/100 ml | $10^8$ | $2 \times 10^4 – 3 \times 10^4$ | $2 \times 10^4 – 3 \times 10^4$ |
| Thermo-tolerant coliforms cfu/100 ml | $3 \times 10^8$ | $2 \times 10^4 – 4 \times 10^4$ | $2 \times 10^4 – 4 \times 10^4$ |

The purification results achieved by the method of the invention were either as good as or better than those achieved by the conventional method, and energy consumption was significantly lower. The energy consumption in treating one cubic meter of water was 0.23 kWh at the municipal waste water treatment plant, and 0.05–0.1 kWh when the method of the invention was used.

EXAMPLE 4

Purification of Household Black Water (Full Scale)

The system comprised five tanks whose total volume was 6.5 m³, the tanks being interconnected in the following order: two anaerobic tanks without a carrier into which the DT-1, DT-2 and DT-5 were added, one aerobic tank whereto a carrier was attached on which the bacteria DT-1, DT-2 and DT-5 were immobilized, and two sedimentation tanks. The temperature was 8–15° C. The flow rate was 0.5–5 m³ of waste water per 24 hours. The aeration was conducted by recycling the water through the carrier. The energy consumption was 0.05–0.5 kWh. The results are shown in Table 4.

TABLE 4

| Parameter | Before treatment | After treatment |
|---|---|---|
| BOD7 mg $O_2$/l | 400–5500 | 3–20 |
| $COD_{Cr}$ mg $O_2$/l | 400–6000 | 40–70 |
| Total nitrogen mg N/l | 100–300 | 1–5 |
| Total phosphorus mg P/l | 10–25 | 0.2–2 |
| Fec. streptococci cfu/100 ml | $10^8–10^9$ | <20 |
| Thermo-tolerant coliforms cfu/100 ml | $10^8–10^9$ | <20 |
| pH | 7–8 | 6.5–7 |

EXAMPLE 5

Purification of Industrial Waste Water Containing Soap and Heavy Metals (Laboratory Scale)

Waste water from a coating metal industry plant was purified by a system whose effective treatment part comprised six anaerobic and twelve aerobic tanks. The bacteria DT-1, DT-2 and DT-5, which were immobilized on a carrier attached by nets, were added to all anaerobic and aerobic tanks. Each tank held 2 l. The entire system comprised 23 tanks whose total volume was 70 l, the tanks being interconnected in the following order: six anaerobic tanks (effective treatment volume), one sedimentation tank, six aerobic tanks (effective treatment volume), one sedimentation tank, six aerobic tanks (effective treatment volume), and two tanks for calcium chloride and sodium hydroxide treatments to precipitate the biomass and heavy metals. Before the treatment, the original waste water was diluted five times by gray water. After the dilution, mineral salts were added as follows: $NH_4^+$ 2–10 mg/l, $NO_3^-$ 5–20 mg/l, $Mg^{2+}$ 2–10 mg/l, $Ca^{2+}$ 0.5–2 mg/l, $SO_4^{2-}$ 1–10 mg/l and $PO_4^{3-}$ 2–20 mg/l. The temperature was 20–35° C. and the flow rate 12 l of water per 24 hours. The results are shown in Table 5.

TABLE 5

| Parameter | Before treatment | After treatment |
|---|---|---|
| $COD_{Cr}$ mg $O_2$/l | 19000–21000 | 100–400 |
| Total phosphorus mg P/l | 19–25 | 0.3–0.7 |
| Aluminium | 5–6 | 0.01–0.02 |
| Chrome | 1.3–1.5 | 0.01–0.02 |
| Copper | 35–40 | 0.03–0.1 |
| Iron | 1–2 | 0.02–0.07 |
| Lead | 23–25 | 0.02–0.09 |
| Nickel | 2–3 | 0.05–0.09 |
| Zinc | 30–60 | 0.003–0.007 |
| pH | 8–9 | 7–7.5 |

EXAMPLE 6

Purification of Household Grey Water for Recycling (Pilot Scale)

The effective part of the system comprised three aerobic tanks whose single volume was 0.2 m³. The entire system comprised six tanks whose total volume was 2.8 m³, the tanks being interconnected in the following order one tank for collecting grey water, three aerobic tanks comprising a fixed carrier on which the bacteria DT-1, DT-2 and DT-5 were immobilized (effective treatment volume), one aerobic tank without a carrier and one sedimentation tank, and, subsequently, a filtering system and a UV-light treatment system. The temperature was 20–35° C. The flow rate was about 1 m³ per 24 hours. The results are shown in Table 6.

TABLE 6

| Parameter | Before treatment | After treatment |
|---|---|---|
| $COD_{Cr}$ mg $O_2$/l | 150–400 | 15–35 |
| Total nitrogen mg N/l | 10–15 | <0.5 |
| Total phosphorus mg P/l | 5–10 | <0.1 |
| Coliforms cfu/100 ml | $1.4–2 \times 10^5$ | 0 |
| pH | 7.5–8.5 | 6.5–7 |

EXAMPLE 7

Purification of Grey Water of a Laundry for Recycling (Pilot Scale)

The effective treatment part of the system comprised two aerobic tanks having the volume of 1 m³, the tanks comprising a swimming carrier on which DT-1, DT-2 and DT-5 were immobilized. The entire system comprised ten tanks whose total volume was 23 m³, the tanks being interconnected in the following order one tank for collecting grey water, two aerobic tanks comprising a swimming carrier (effective treatment volume), one sedimentation tank, three aerobic tanks comprising a fixed carrier with its bacteria (effective treatment volume), one aerobic tank without a carrier, and two sedimentation tanks. The temperature of the water was 20–35° C., the flow rate 1 m³ of waste water per 24 hours. The results are shown in Table 7.

TABLE 7

| Parameter | Before treatment | After treatment |
|---|---|---|
| $COD_{Cr}$ mg $O_2$/l | 200–450 | 25–35 |
| Total phosphorus mg P/l | 1–2 | <0.1 |
| pH | 8.5–9 | 7–8 |

EXAMPLE 8

Increase of Immobilized Biomass

Biomass of strains DT-1, DT-2, DT-5, DT-6, DT-10, DT-12 and DT-13 was produced and immobilized on a carrier as set forth in Example 1, and the amount of biomass on the carrier was weighed. The weight of one disc of the carrier was 72±1 g. When DT-1, DT-2 and DT-5 were immobilized on the carrier, the weight of one disc of the carrier was 119±13, i.e. the wet weight of the biomass was 47±11 g per disc. When all seven bacterial strains were immobilized on the carrier, the weight of one disc of carrier was 172±16, i.e. the wet weight of the biomass was 91±16. The results show that DT-6, DT-10, DT-12 and DT-13 increased the immobilized biomass about twofold.

What is claimed is:

1. A method of purifying waste water, characterized in that the water is biologically purified by a mixed population comprising the microorganisms Bacillus sp. DT-1 having the deposit number DSM 12560, Pseudomonas azelaica DT-2 having the deposit number DSM 12561, and Rhizobium sp. DT-5 having the deposit number DSM 12562, or progeny thereof.

2. A method as claimed in claim 1, characterized by purifying seep water, grey water, black water, industrial waste water and waste water from laundries.

3. A method as claimed in claim 1, characterized in that necessary biomass for the purification is produced in a non-sterilized growth medium comprising tap water and about 0.5–4 g/l of soap.

4. A method as claimed in claim 1, characterized in that the water is also purified by one or more microorganisms from the group Pseudomonas azelaica DT-6 having the deposit number DSM 13516, Azospirillium sp. DT-10 having the deposit number DSM 13517, Ancylobacter aquaticus DT-12 having the deposit number DSM 13518, and Xanthobacter sp; DT-13 having the deposit number DSM 13519, and progeny thereof.

5. Bacillus sp. DT-1 having the deposit number DSM 12560 and progeny thereof.

6. Pseudomonas azelaica DT-2 having the deposit number DSM 12561 and progeny thereof.

7. Rhizobium sp. DT-5 having the deposit number DSM 12562 and progeny thereof.

8. Pseudomonas azelaica DT-6 having the deposit number DSM 13516 and progeny thereof.

9. Azospirillium sp. DT-10 having the deposit number DSM 13517 and progeny thereof.

10. Ancylobacterium aquaticus DT-12 having the deposit number DSM 13518 and progeny thereof.

11. Xanthobacter sp. DT-13 having the deposit number DSM 13519 and progeny thereof.

12. A bacterial mixed population, characterized by comprising Bacillus sp. DT-1 having the deposit number DSM 12560, Pseudomonas azelaica DT-2 having the deposit number DSM 12561, and/or Rhizobium sp. DT-5 having the deposit number DSM 12562, and progeny thereof.

13. A bacterial mixed population as claimed in claim 12, characterized by further comprising Pseudomonas azelaica DT-6 having the deposit number DSM 13516, Azospirillium sp. DT-10 having the deposit number DSM 13517, Ancylobacter aquaticus DT-12 having the deposit number DSM 13518, and/or Xanthobacter sp. DT-13 having the deposit number DSM 13519, and progeny thereof.

14. Use of a bacterial mixed population as claimed in claim 12 in purifying waste water.

15. A bioreactor, characterized by comprising the microorganisms Bacillus sp. DT-1 having the deposit number DSM 12560, Pseudomonas azelaica DT-2 having the deposit number DSM 12561, and Rhizobium sp. DT-5 having the deposit number DSM 12562, or progeny thereof.

16. A bioreactor as claimed in claim 15, characterized by further comprising one or more microorganisms from the group Pseudomonas azelaica DT-6 having the deposit number DSM 13518, Azospirillium sp. DT-10 having the deposit number DSM 13517, Ancylobacter aquaticus DT-12 having the deposit number DSM 13518, and Xanthobacter sp. DT-13 having the deposit number DSM 13519, or progeny thereof.

17. A bioreactor as claimed in claim 16, characterized by comprising all said seven bacterial strains.

18. A bioreactor as claimed in claim 15, characterized by comprising one or more separating walls arranged so as to force water to circulate in the reactor.

19. A bioreactor as claimed in claim 18, characterized in that the bacteria are immobilized on a plastic carrier medium whose specific density is about 0.8 g/cm³.

* * * * *